United States Patent [19]
Yao

[11] Patent Number: 5,591,983
[45] Date of Patent: Jan. 7, 1997

[54] MULTIPLE LAYER MULTILEAF COLLIMATOR

[75] Inventor: Jonathan Y. Yao, Pleasant Hill, Calif.

[73] Assignee: Siemens Medical Systems, Inc., New Jersey, Calif.

[21] Appl. No.: 491,322

[22] Filed: Jun. 30, 1995

[51] Int. Cl.⁶ .............................. G21K 1/04; G02B 5/00; H01J 1/52
[52] U.S. Cl. ........................................ 250/505.1; 378/152
[58] Field of Search ........................ 250/505.1; 378/153, 378/152

[56] References Cited

U.S. PATENT DOCUMENTS

| | | | |
|---|---|---|---|
| 4,463,266 | 7/1984 | Brahme | 250/505.1 |
| 4,739,173 | 4/1988 | Blosser et al. | 250/505.1 |
| 4,868,844 | 9/1989 | Nunan | 378/152 |
| 4,987,309 | 1/1991 | Klasen et al. | 250/492.1 |
| 5,012,506 | 4/1991 | Span et al. | 378/152 |
| 5,160,847 | 11/1992 | Leavitt et al. | 250/505.1 |
| 5,165,106 | 11/1992 | Barthelmes et al. | 250/505.1 |
| 5,166,531 | 11/1992 | Huntzinger | 250/505.1 |
| 5,231,655 | 7/1993 | Wei et al. | 378/147 |
| 5,351,280 | 9/1994 | Swerdloff et al. | 250/505.1 |

Primary Examiner—Bruce C. Anderson
Attorney, Agent, or Firm—Lawrence C. Edelman

[57] ABSTRACT

A multiple layer multileaf collimator for shaping a radiation beam. The collimator comprises first and second layers of a plurality of elongated radiation blocking leaves. The leaves of each layer are arranged adjacent one another so as to form two opposed rows of adjacently positioned leaves and are movable in a longitudinal direction (Y) which is generally traverse to the direction of the beam so as to define a radiation beam shaping field between the opposed ends of the leaves. The layers are arranged one above another in the beam direction and offset in a lateral direction (X) generally transverse to the beam direction and orthogonal to the longitudinal direction (Y) so that spaces between adjacent leaves of the first and second layers are positioned over and under, respectively, leaves of the second and first layers, respectively.

14 Claims, 4 Drawing Sheets

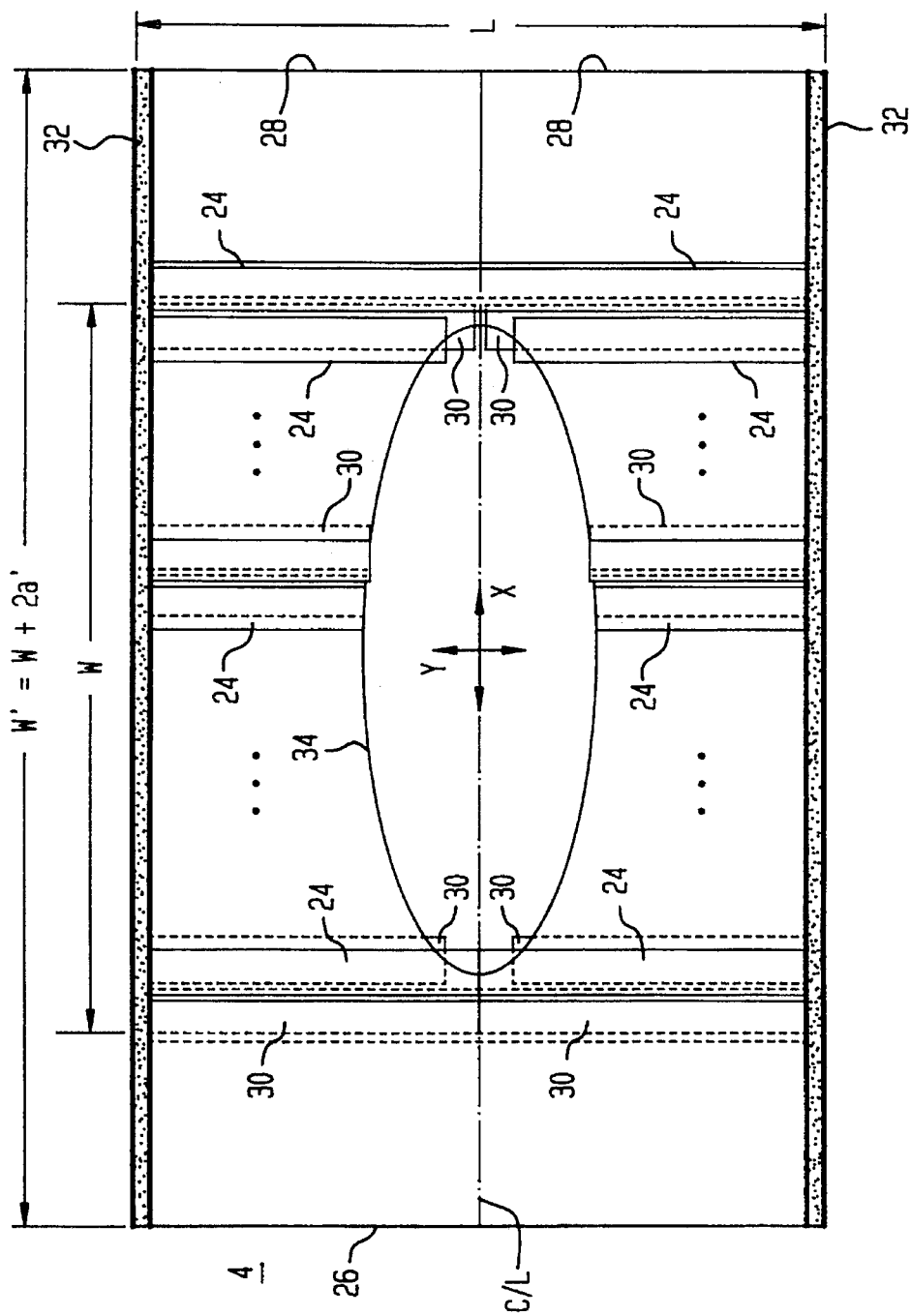

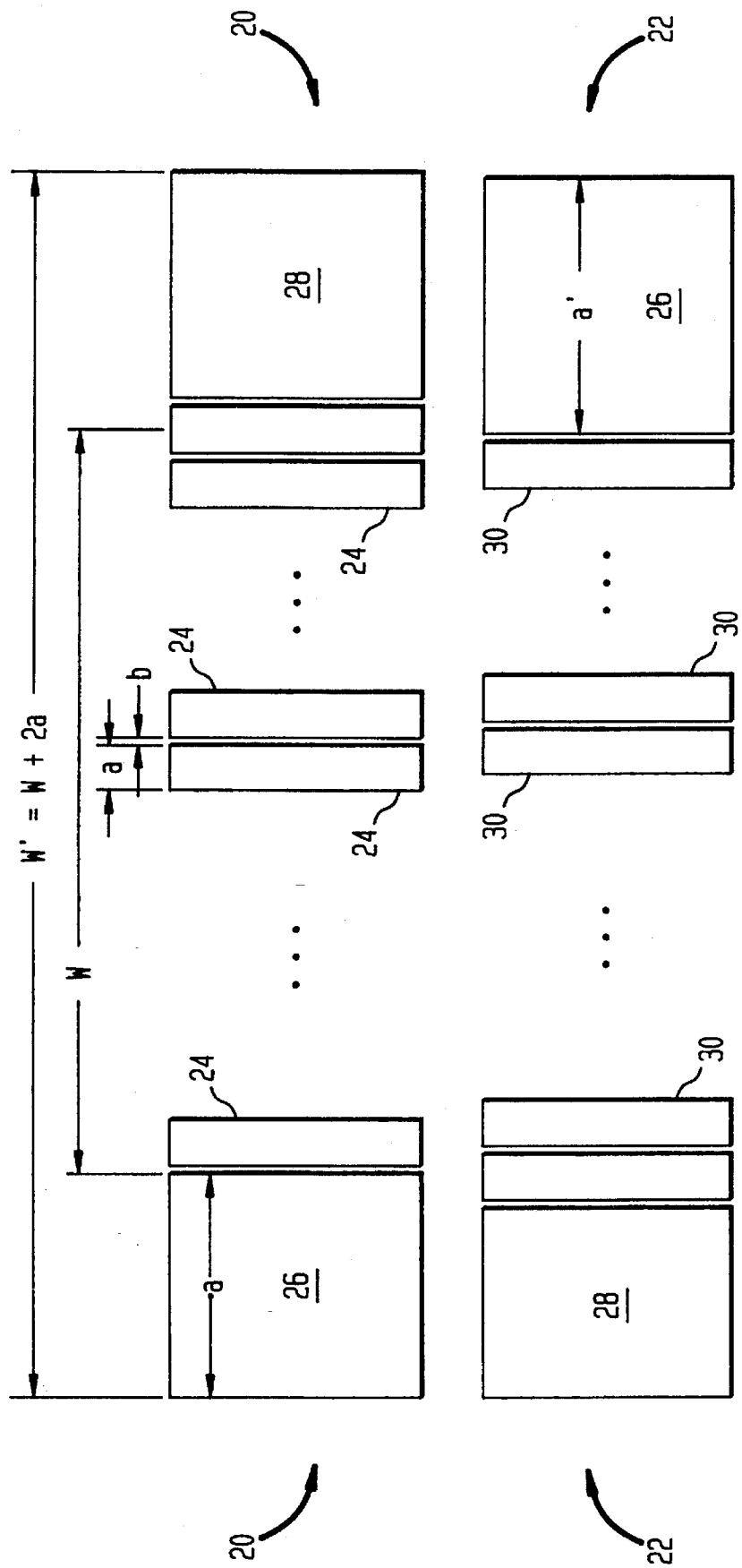

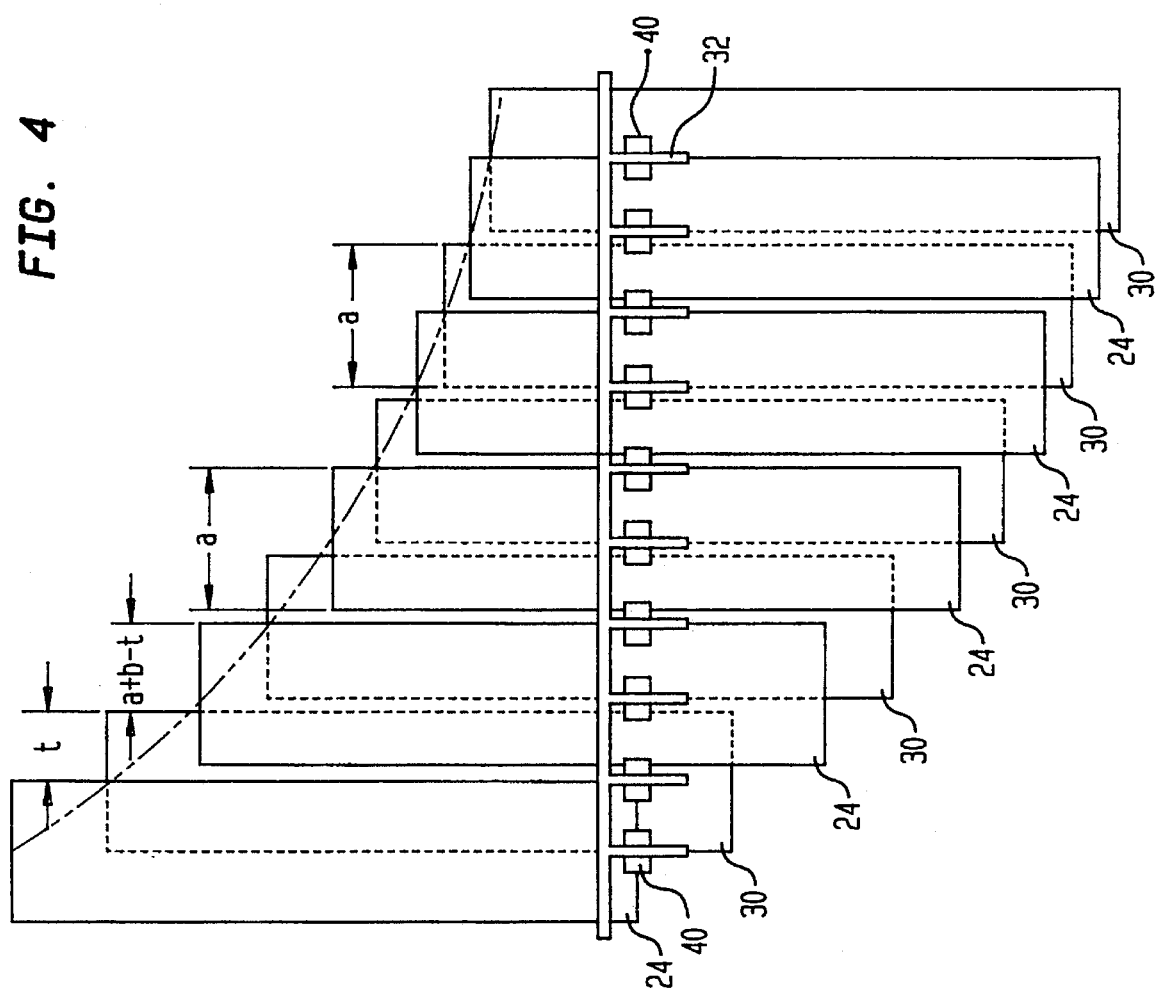

MULTIPLE LAYER MULTILEAF COLLIMATOR

BACKGROUND OF THE INVENTION

1. Field of the Invention

The invention described herein involves a multiple layer multileaf collimator for use during radiation treatment to shape and control the spatial distribution of a radiation beam.

2. Description of the Prior Art

During conventional radiation therapy treatment a radiation beam of varying angles and intensities is directed at a tumor in a patient. Typical treatment field shapes currently used (square, rectangular, or a modification thereof) result in a three-dimensional treatment volume which unfortunately includes segments of normal tissue and organs. The normal tissue and organs located in the path of the radiation beam must be taken into account for obvious safety reasons, thereby limiting the dose that can be delivered to the tumor. Cure rates for many tumors are a sensitive function of the dose they receive. The dose delivered to the tumor can be increased if the amount of exposed normal tissue or organs is reduced. Various methods of making the treatment volume conform more closely to the shape of the tumor volume are being developed, with the goal of delivering a higher dose to the tumor with less damage to normal tissue and organs, resulting in a positive effect on the health of the patient. Various approaches are being developed, including moving solid jaw-blocks during treatment, scanning the radiation beam over the volume to be treated, and using a multileaf collimator to create an irregularly shaped field related to the shape of the tumor.

Multileaf collimators can be used in a manner similar to conventional solid jaw-blocks. In addition, each individual segment or leaf in a multileaf collimator can be positioned independently, allowing the user to create an infinite amount of irregularly shaped fields. The radiation beam is directed between the ends of opposing arrays of the radiation blocking collimator leaves, thereby shaping the beam to closely match the shape of the desired treatment area, while shielding the normal tissue and organs.

U.S. Pat. No. 5,166,531 issued to Hunziger on Nov. 24, 1992 discloses a multileaf collimator arrangement positioned about the central axis of a radiation emitting head for shaping an emitted radiation beam. In place of the opposing solid jaw-blocks found in the standard collimator, one finds two opposing arrays of side-by-side elongated radiation blocking collimator leaves. Each leaf in each opposing array can be moved longitudinally towards or away from the central axis of the beam, thus defining a desired shape through which the radiation beam will pass.

Because the adjoining leaves must be tightly positioned side-by-side in order to minimize radiation leakage between the leaves, friction is an inherent problem, creating complications in maintaining a set position of one leaf while re-positioning an adjacent leaf, such repositioning being frequently required in conformal therapy. If friction between the adjacent leaves is reduced by providing a looser fit between adjacent leaves, unacceptable radiation leakage through spaces between the adjacent leaves will result. On the other hand, maintaining a tight leaf fit between the adjacent leaves and providing a teflon or other lubricating layer in the contact area of the adjacent leaves is also not an acceptable solution because the lower density of the lubricating layer, as compared to the high density of the collimator leaves, will allow an unacceptable amount of radiation leakage to occur.

It is an object of the present invention provide a multileaf collimator arrangement which not only solves the radiation leakage and friction problems mentioned above, but also improves the ability to accurately define the desired shape through which the radiation beam passes.

It is a further object of the invention to reduce the overall manufacturing cost of multileaf collimators.

It is an even further object of the invention to provide a multileaf collimator arrangement which maintains the ability to create larger rectangular treatment fields.

SUMMARY OF THE INVENTION

The present invention comprises a multiple layer multileaf collimator for shaping a radiation beam. The collimator includes first and second layers of a plurality of elongated radiation blocking leaves. The leaves of each layer are arranged adjacent one another so as to form two opposed rows of adjacently positioned leaves and are movable in a longitudinal direction (Y) which is generally traverse to the direction of the beam so as to define a radiation beam shaping field between the opposed ends of the leaves. The layers are arranged one above another in the beam direction and offset in a lateral direction (X) which is generally transverse to the beam direction and orthogonal to the longitudinal direction (Y) so that spaces between adjacent leaves of the first and second layers are positioned over and under, respectively, leaves of the second and first layers, respectively.

As a result of the advantageous positioning of the spaces between leaves of one layer with the leaves of the other layer, a looser fit between adjacent leaves can be tolerated. The looser fit solves the mechanical design problem caused by the dilemma between a tight fit for reducing the radiation leakage between adjacent leaves and the complications presented thereby of providing a positioning system wherein the leaves are independently positionable and thereafter maintain their position. The ability to accurately position the leaves to conform to an irregular shape is also improved. Additionally, the modular design of the arrangement can reduce the manufacturing and maintenance costs.

These advantages as well as other features of the present invention will be apparent from the description of the preferred embodiment of the invention and the claims.

For a fuller understanding of the present invention, reference should now be made to the following detailed description and the accompanying drawings.

BRIEF DESCRIPTION OF THE DRAWINGS

FIG. 2 illustrates a multiple layer leaf collimator constructed in accordance with the principles of the present invention, as seen from the beam source of the radiation therapy apparatus;

FIG. 3 illustrates a side view of the collimator shown in FIG. 2; and

FIG. 4 illustrates a close-up view of a portion of the collimator arrangement shown in FIG. 2.

DETAILED DESCRIPTION OF THE PREFERRED EMBODIMENT

Figure 1:
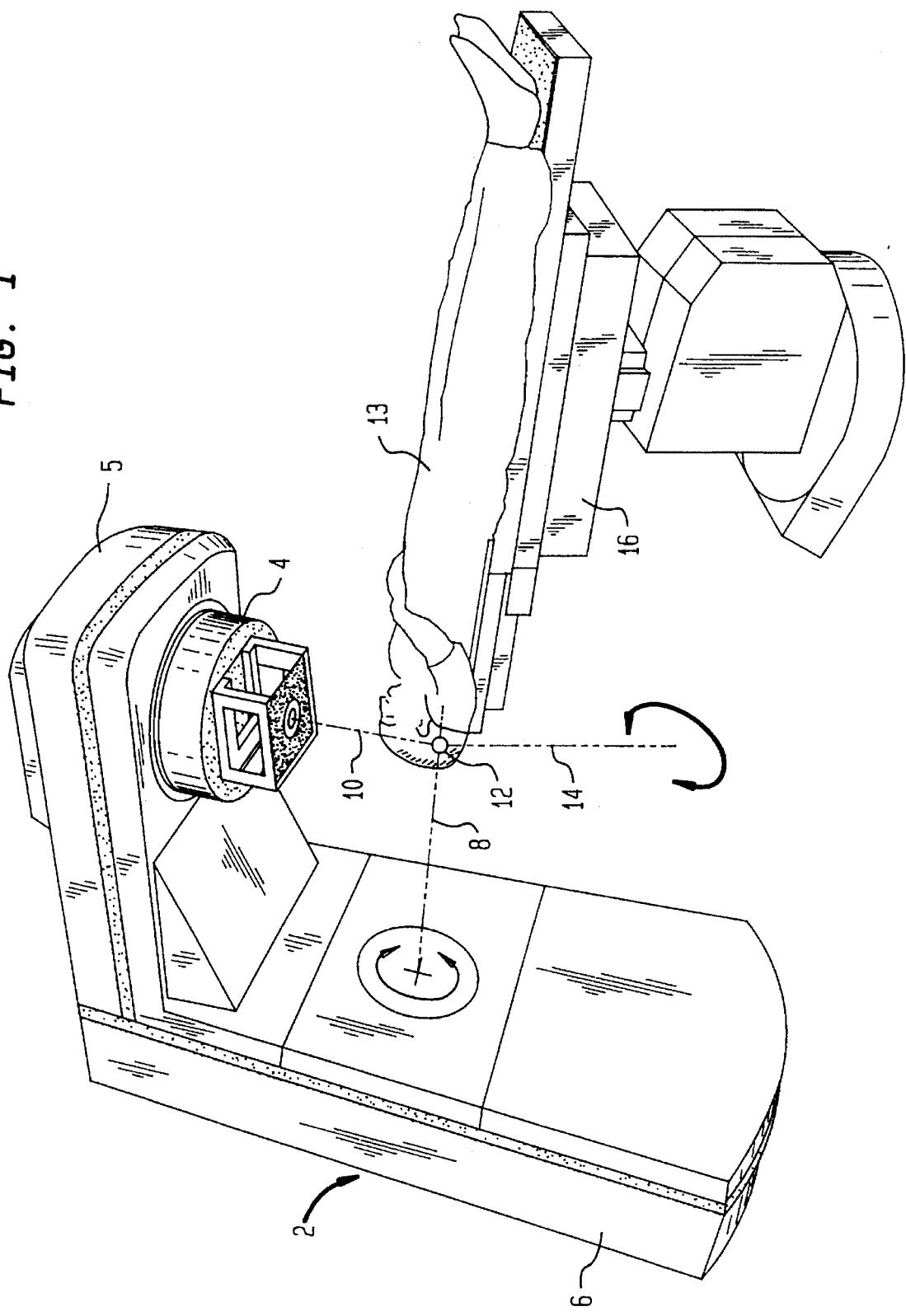
FIG. 1 illustrates a perspective view of a radiation therapy apparatus including a multileaf collimator assembly constructed in accordance with the principles of the present invention.

FIG. 1 shows a part of a radiation therapy unit 2 of conventional design, in which a multileaf collimator 4 constructed in accordance with the principles of the invention is used. The radiation therapy unit 2 comprises a gantry 6 which can be swiveled around a horizontal axis of rotation 8 in the course of a therapeutic treatment. Collimator 4 is fastened to a projection 5 of gantry 6. Projection 5 includes a linear accelerator (not shown) for generating a radiation beam 10 which is emitted from a central axis of the therapy unit 2 which is coincident with a central axis of collimator 4. Either electron radiation or photon radiation (gamma radiation) can be used for therapy. During treatment, beam 10 is trained on a zone 12 of a patient 13 to be treated and which lies in the isocenter of the gantry rotation. The rotational axis 8 of the gantry 6, the rotational axis 14 of a treatment table 16 and the beam axis 10 all intersect at the isocenter.

As illustrated in FIGS. 2 and 3, the multiple layer collimator 4 of the present invention comprises two identical layers, an upper layer 20 and a lower layer 22, of pairs of opposed multiple leaves. As shown in the side view of FIG. 3, the top layer 20 comprises a middle section having a plurality of relatively narrow leaves 24 positioned in a side-by-side relationship, which is flanked on its left side by a relatively wide trimmer leaf 26 and on its right side by a relatively wide end leaf 28. The construction of bottom layer 22 is a mirror image of layer 20 and therefor common reference numbers are used for leaves 26 and 28, however, since in the middle section of layers 20 and 22 the narrow leaves are physically overlapping, the narrow leaves of layer 22 are referred by reference number 30.

As shown in FIG. 2, wherein top layer 20 is shown in solid lines, bottom layer 22 is shown in dashed lines and a support frame 32 is shown in thick solid lines, frame 32 supports each of leaves 24 and 28 of top layer 20 and each of leaves 30 and 28 of lower layer 22 in a paired opposed relationship, so that they are independently movable in their longitudinal dimension into and out of beam axis 10 (the Y direction shown in FIG. 2), thereby allowing a user to create an infinite number of irregular and rectangular treatment fields 34 through which the radiation beam will pass. The size of the treatment field is limited in the X direction to the distance W between the inner edges of the opposed pairs of leaves 28 of layers 20 and 22 when fully closed, and in the Y direction to the distance L between the narrow leaves 24 or 30 when fully open. Thus, in general the maximum size field is a rectangle of dimension W×L. Note, as shown in FIG. 2, and as will be described in detail later, trimmer leaf 26 extends across the full width L of support frame 32, and is movable in the X direction for defining the ends of rectangular treatment fields. Also note that in FIG. 2 the leftmost leaves 24 and 30 are shown fully closed, and the second leftmost leaf 24 is shown partially open.

The operation of leaves 24 and 28 of layer 20 (or leaves 30 and 28 of layer 22) for creating a treatment field is as is conventional in prior art single layer multileaf collimator arrangements.

However, as more clearly shown in FIG. 3, for the multiple layer multileaf arrangement constructed in accordance with the principles of the invention, the leaves of each layer are not required to be manufactured to tolerances as close as those in the prior art so as to maintain a radiation blocking fit therebetween. Multileaf collimator arrangements constructed in accordance with the present invention are permitted a relatively wide interleaf spacing "b", which allows a relatively large manufacturing tolerance for the leaves and the assembly of each layer of the collimator. This significantly reduces the manufacturing cost of the leaves, as well as their completed assembly cost. Additionally, the increased interleaf spacing reduces the interleaf friction, thereby solving the previously noted positioning/repositioning problem.

In order to prevent radiation leakage from between the leaves from reaching the patient, in accordance with the principles of the invention, lower layer 22 is positioned laterally offset from the axis of beam 10 as compared with the position of layer 20, so that underneath each space "b" between adjacent leaves 24 of layer 20 their is a leaf 30 of lower layer 22. Of course, the thickness (in the beam direction) of each leaf is designed to have sufficient density to safely block the treatment beam. An additional advantage of the present invention is that due to the offsetting relationship between the upper and lower leaves, the spatial resolution available for creating the edges of the treatment fields is increased from a (the width of a narrow leaf) to (a+b)/2.

In accordance with another aspect of the invention, although leaves 24, 30, and 28 move in their longitudinal direction and only extend across one-half of treatment field 34, as previously noted, trimmer leaves 26 extend across the full width of support frame 32 (as more clearly shown at the left side of FIG. 2 for leaf 26 of layer 20), and are movable in their lateral, as opposed to their longitudinal, dimension. As such, they are positionable into and out of the axis of beam 10 in the X direction shown in FIG. 2. Thus, trimmer leaves 26 of layers 20 and 22 can be used to create left and right edges, respectively, of a rectangular treatment field 34 in the event that it is desired to create a rectangular treatment field having a width greater than the combined lateral dimension of all the adjacent narrow leaves 24 (or 30) and the end leaves 28. When using a trimmer leaf 26 to define one end of a rectangular treatment field, since any leaves adjacent leaf 26 will prevent its movement in the X direction, only those leaves 24,28 or 30,28 needed to define the field end opposing trimmer leaf 26 are fully extended, and all of the remaining leaves in that layer are fully retracted. The opposed leaves in the other of the layers (which are either above or below) can be used to define the length L of the treatment field.

For creating a small rectangular field, a necessary number of adjacent narrow leaves 24 and 30 between the wide leaves 28 would be retracted, and the remainder of the leaves 24, 30 and 28 would be fully extended. For a creating a larger rectangular field, the narrow and wide leaves 8, 30, and 28 would be fully retracted, and the trimmer leaves 26 can be moved outward, thereby enlarging the X dimension to as much as W'=W+2a' (where a' is the width of a trimmer leaf 26).

FIG. 4 illustrates in greater detail a portion of the top view of FIG. 2. As functionally show therein, frame 32 includes a plurality of motors 40 mounted thereon which are used in a conventional manner to individually position the leaves 24, 30 and 28 of the collimator into and out of the radiation beam for controllably defining the treatment field. One example of drive means (not shown) suitable for this is an individually driven worm gear for individually engaging a toothed track or floating nut mounted on each leaf. A similar arrangement can be used for driving the trimmer leaves 26. Details of one such prior art leaf driving means are provided in U.S. Pat. No. 5,160,847, issued Nov. 3, 1992 to Leavitt, et al.

It is noted that due to the modular nature of a multi-leaf collimator constructed in accordance with the principles of the present invention, the manufacturing and assembly cost of the present design is significantly reduced as compared with prior art designs. That is, collimators in accordance with the present design are constructed from four identical leaf array jaws (and two end trimmers); i.e., two sets of wide leaves 28 (one set in each of layers 20 and 6) and two sets of narrow leaves (one set of leaves 24 in layer 20 and one set of leaves 30 in layer 6). The jaws of each of these sets can be manufactured and tested independently and later assembled together, thereby providing the above-noted cost reductions. Additionally, each part may be serviced and replaced, if necessary, separately, thereby reducing potential maintenance costs.

Thus, what has been shown and described herein is a novel radiation treatment system that both overcomes problems inherent in the prior art and improves the functionality of multileaf collimators. Changes, modifications, variations and other uses and applications of the subject invention will become apparent to those skilled in the art after considering this specification and its accompanying drawings, which disclose preferred embodiments thereof. For example, in an alternative embodiment the trimmer leaves could be positioned in a separate, third leaf layer, for example one nearer to the source of the radiation beam. In this alternative embodiment, trimmer leaves 26 in layer 20 and 22 could be replaced with leaves similar in structure and operation to leaves 28. Additionally, various design changes can be made to the shape of the individual leaves, etc. All such changes, modifications, variations and other uses and applications which do not depart from the spirit and scope of the invention are deemed to be covered by this patent, which is limited only by the claims which follow.

What I claim is:

1. A radiation emitting apparatus, comprising:
   a source of radiation for providing a substantially unshaped radiation beam in a given beam direction, and
   a collimator for shaping said radiation beam, said collimator comprising, first and second layers of a plurality of elongated radiation blocking leaves, frame means for supporting said leaves, and moving means for moving said leaves, said leaves of each layer being arranged adjacent one another so as to form two opposed rows of adjacently positioned leaves and being movable by said moving means in a longitudinal direction (Y) which is generally traverse to the beam direction so as to define a radiation beam shaping field between the opposed ends of the leaves, and said layers being arranged one above another in the beam direction and offset in a lateral direction (X) generally transverse to the beam direction and orthogonal to the longitudinal direction (Y) so that spaces between adjacent leaves of said first and second layers are positioned over and under, respectively, leaves of said second and said first layers, respectively;
   wherein each row of said collimator leaves comprises a plurality of adjacently positioned relatively narrow width leaves bounded on at least one end with a relatively wider width end leaf which is also movable in the longitudinal direction.

2. The radiation emitting apparatus of claim 1, wherein each row of said collimator leaves is bounded at its other end by a relatively wider width trimmer leaf movable in the lateral direction.

3. The radiation emitting apparatus of claim 2, wherein each of said leaves that are movable in said longitudinal direction are able to be retracted by an amount sufficient to permit said trimmer leafs to be individually extendable into said radiation beam so as to define a width for said radiation field.

4. A radiation emitting apparatus, comprising:
   a source of radiation for providing a substantially unshaped radiation beam in a given beam direction, and
   a collimator for shaping said radiation beam, said collimator comprising, first and second layers of a plurality of elongated radiation blocking leaves, frame means for supporting said leaves, and moving means for moving said leaves, said leaves of each layer being arranged adjacent one another so as to form two opposed rows of adjacently positioned leaves and being movable by said moving means in a longitudinal direction (Y) which is generally traverse to the beam direction so as to define a radiation beam shaping field between the opposed ends of the leaves, and said layers being arranged one above another in the beam direction and offset in a lateral direction (X) generally transverse to the beam direction and orthogonal to the longitudinal direction (Y) so that spaces between adjacent leaves of said first and second layers are positioned over and under, respectively, leaves of said second and said first layers, respectively;
   wherein each of said collimator leaves comprises an identical arrangement of collimator leaves; and
   wherein each layer of collimator leaves comprises a central plurality of a set of opposed and adjacently positioned relatively narrow width leaves bounded at one end with a set of a relatively wider width leaf.

5. The radiation emitting apparatus of claims 4, wherein an other end of said narrow width leaves is bounded with a relatively wider width leaf movable in the lateral direction.

6. The radiation emitting apparatus of claims 5, wherein said first and second layers of said collimator are positioned so that the order of said leaf arrangement in said first layer is a mirror image of the order of the leaf arrangement in said second layer.

7. A radiation emitting apparatus, comprising:
   a source of radiation for providing a substantially unshaped radiation beam in a given beam direction, and
   a collimator for shaping said radiation beam, said collimator comprising, first and second layers of a plurality of elongated radiation blocking leaves, frame means for supporting said leaves, and moving means for moving said leaves, said leaves of each layer being arranged adjacent one another so as to form two opposed rows of adjacently positioned leaves and being movable by said moving means in a longitudinal direction (Y) which is generally traverse to the beam direction so as to define a radiation beam shaping field between the opposed ends of the leaves, and said layers being arranged one above another in the beam direction and offset in a lateral direction (X) generally transverse to the beam direction and orthogonal to the longitudinal direction (Y) so that spaces between adjacent leaves of said first and second layers are positioned over and under, respectively, leaves of said second and said first layers, respectively;
   wherein each of said collimator leaves comprises an identical arrangement of collimator leaves; and
   wherein said first and second layers of said collimator are positioned so that the order of said leaf arrangement in said first layer is a mirror image of the order of the leaf arrangement in said second layer.

8. A multileaf collimator for use in a radiation system providing a radiation beam in a given beam direction, comprising:

a first layer of a plurality of elongated radiation blocking leaves, said leaves being arranged adjacent one another so as to form two opposed rows of adjacently positioned leaves and being movable in a longitudinal direction (Y) which is generally traverse to the beam direction so as to define a radiation beam shaping field between the opposed ends of the leave;

a second layer of a plurality of elongated radiation blocking leaves, said leaves of said second layer also being arranged adjacent one another so as to form two opposed rows of adjacently positioned leaves and being movable in a longitudinal direction (Y) which is generally traverse to the beam direction so as to define a radiation beam shaping field between the opposed ends of the leaves;

frame means for supporting said leaves of said first layer and said leaves of said second layer; and moving means for moving said leaves of said first layer and said leaves of said second layer in the longitudinal direction;

wherein said first and second layers are arranged one above another in the beam direction and are offset in a lateral direction (X) generally transverse to the beam direction, so that spaces between adjacent leaves in said first and second layers are positioned over and under, leaves of said second and said first layers; and wherein each row of said collimator leaves comprises a plurality of adjacently positioned relatively narrow width leaves bounded on at least one end with a relatively wider width end leaf which is also movable in the longitudinal direction.

9. The radiation emitting apparatus of claim 8, wherein each row of said collimator leaves is bounded at its other end by a relatively wider width trimmer leaf movable in the lateral direction.

10. The radiation emitting apparatus of claim 9, wherein each of said leaves that are movable in said longitudinal direction are able to be retracted by an amount sufficient to permit said trimmer leafs to be individually extendable into said radiation beam so as to define a width for said radiation field.

11. A multileaf collimator for use in a radiation system providing a radiation beam in a given beam direction, comprising:

a first layer of a plurality of elongated radiation blocking leaves, said leaves being arranged adjacent one another so as to form two opposed rows of adjacently positioned leaves and being movable in a longitudinal direction (Y) which is generally traverse to the beam direction so as to define a radiation beam shaping field between the opposed ends of the leaves;

a second layer of a plurality of elongated radiation blocking leaves, said leaves of said second layer also being arranged adjacent one another so as to form two opposed rows of adjacently positioned leaves and being movable in a longitudinal direction (Y) which is generally traverse to the beam direction so as to define a radiation beam shaping field between the opposed ends of the leaves;

frame means for supporting said leaves of said first layer and said leaves of said second layer; and moving means for moving said leaves of said first layer and said leaves of said second layer in the longitudinal direction;

wherein said first and second layers are arranged one above another in the beam direction and are offset in a lateral direction (X) generally transverse to the beam direction, so that spaces between adjacent leaves in said first and second layers are positioned over and under, respectively, leaves of said second and said first layers;

wherein each of said collimator layers comprises an identical arrangement of collimator leaves; and wherein each layer of collimator leaves comprises a central plurality of a set of opposed and adjacently positioned relatively narrow width leaves bounded at one end with a set of a relatively wider width leaf.

12. The radiation emitting apparatus of claim 11, wherein an other end of said narrow width leaves is bounded with a relatively wider width leaf movable in the lateral direction.

13. The radiation emitting apparatus of claims 12, wherein said first and second layers of said collimator are positioned so that the order of said leaf arrangement in said first layer is a mirror image of the order of the leaf arrangement in said second layer.

14. A multileaf collimator for use in a radiation system providing a radiation beam in a given beam direction, comprising:

a first layer of a plurality of elongated radiation blocking leaves, said leaves being arranged adjacent one another so as to form two opposed rows of adjacently positioned leaves and being movable in a longitudinal direction (Y) which is generally traverse to the beam direction so as to define a radiation beam shaping field between the opposed ends of the leaves;

a second layer of a plurality of elongated radiation blocking leaves, said leaves of said second layer also being arranged adjacent one another so as to form two opposed rows of adjacently positioned leaves and being movable in a longitudinal direction (Y) which is generally traverse to the beam direction so as to define a radiation beam shaping field between the opposed ends of the leaves;

frame means for supporting said leaves of said first layer and said leaves of said second layer; and moving means for moving said leaves of said first layer and said leaves of said second layer in the longitudinal direction;

wherein said first and second layers are arranged one above another in the beam direction and are offset in a lateral direction (X) generally transverse to the beam direction, so that spaces between adjacent leaves in said first and second layers are positioned over and under, respectively leaves of said second and said first layers;

wherein each of said collimator layers comprises an identical arrangement of collimator leaves; and wherein said first and second layers of said collimator are positioned so that the order of said leaf arrangement in said first layer is a mirror image of the order of the leaf arrangement in said second layer.

\* \* \* \* \*